United States Patent
Zou et al.

(10) Patent No.: US 12,281,094 B2
(45) Date of Patent: Apr. 22, 2025

(54) PREPARATION METHOD OF RACEMIC NICOTINE

(71) Applicant: SHENZHEN ZINWI BIO-TECH CO., LTD, Guangdong (CN)

(72) Inventors: Jun Zou, Guangdong (CN); Yang Zou, Guangdong (CN); Meisen Liu, Guangdong (CN); Weixian Luo, Guangdong (CN)

(73) Assignee: SHENZHEN ZINWI BIO-TECH CO., LTD, Guangdong (CN)

( * ) Notice: Subject to any disclaimer, the term of this patent is extended or adjusted under 35 U.S.C. 154(b) by 803 days.

(21) Appl. No.: 17/547,254

(22) Filed: Dec. 10, 2021

(65) Prior Publication Data

US 2023/0075688 A1    Mar. 9, 2023

Related U.S. Application Data

(63) Continuation of application No. PCT/CN2021/115397, filed on Aug. 30, 2021.

(30) Foreign Application Priority Data

Jul. 28, 2021 (CN) .......................... 202110858727.3

(51) Int. Cl.
*C07D 401/04* (2006.01)
(52) U.S. Cl.
CPC .................................. *C07D 401/04* (2013.01)
(58) Field of Classification Search
CPC .................................................. C07D 401/04
See application file for complete search history.

(56) References Cited

PUBLICATIONS

Wagner "Recent advances in the synthesis of nicotine and its derivatives" Tetrahedron 63 (2007) 8065-8082.*
Ye "Research Progress in the Pharmacological Effects and Synthesis of Nicotine" ChemistrySelect 2022, 7, e202104425, 1-16 (First published: Mar. 23, 2022).*
Kaiser "Amide activation: an emerging tool for chemoselective synthesis" Chem. Soc. Rev., 2018, 47, 7899.*
McNab "3-Hydroxypyrroles [Pyrrol-3(2H)-ones]" J . Chem. Soc., Chem. Commun., 1985, 213-214.*
Miao "Aromatization-driven deconstructive functionalization of spiro dihydroquinazolinones via dual photoredox/nickel catalysis" Chem. Sci., 2024, 15, 8993.*
Ian R. Baxendale et al., "Synthesis of nornicotine, nicotine and other functionalised derivatives using solid-supported reagents and scavengers," Journal of the Chemical Society, Perkin Transactions 1, Issue 2, Jan. 2002, pp. 143-154.
Kun Huang et al., "A new and efficient approach to the synthesis of nicotine and anabasine analogues," Journal of Heterocyclic Chemistry, vol. 46, No. 6, Nov. 2009, pp. 1-21.

* cited by examiner

*Primary Examiner* — David K O'Dell
(74) *Attorney, Agent, or Firm* — JCIP GLOBAL INC.

(57) ABSTRACT

The present application provides a preparation method of racemic nicotine, including the following steps: Nicotinyl chloride and methylamine are reacted under alkaline conditions to obtain methylnicotinamide, then condensed with monochloroacetone to obtain N-methyl-N-(2-oxopropyl) nicotinamide, then self-aldol condensed to obtain 1-methyl-5-(pyridin-3-yl)-1,2-dihydro-3H-pyrrol-3-one, and finally reduced to obtain racemic nicotine.

10 Claims, No Drawings

PREPARATION METHOD OF RACEMIC NICOTINE

CROSS-REFERENCE TO RELATED APPLICATION

This application is a continuation of international application of PCT application serial no. PCT/CN2021/115397 filed on Aug. 30, 2021, which claims the priority benefit of China application no. 202110858727.3, filed on Jul. 28, 2021. The entirety of each of the above mentioned patent applications is hereby incorporated by reference herein and made a part of this specification.

BACKGROUND

Technical Field

Nicotine, as one of the main components of e-cigarette, mainly comes from tobacco extract and artificial chemical synthesis. Purified nicotine extracted from plants such as tobacco tends to be affected by raw materials and climate, etc, and thus is difficult to be produced by large-scale industrial production. Furthermore, it contains other carcinogenic tobacco compound impurities besides nicotine, which affects the health of an e-cigarette smoker. However, synthetic nicotine by artificial chemical method can effectively avoid the above deficiencies of extracting nicotine from plants such as tobacco.

A method for preparing nicotine from 3-bromopyridine as raw materials is reported in the literature (Journal of Heterocyclic Chemistry, 2009, 46(6), 1252-1258), as shown in Reaction formula 1:

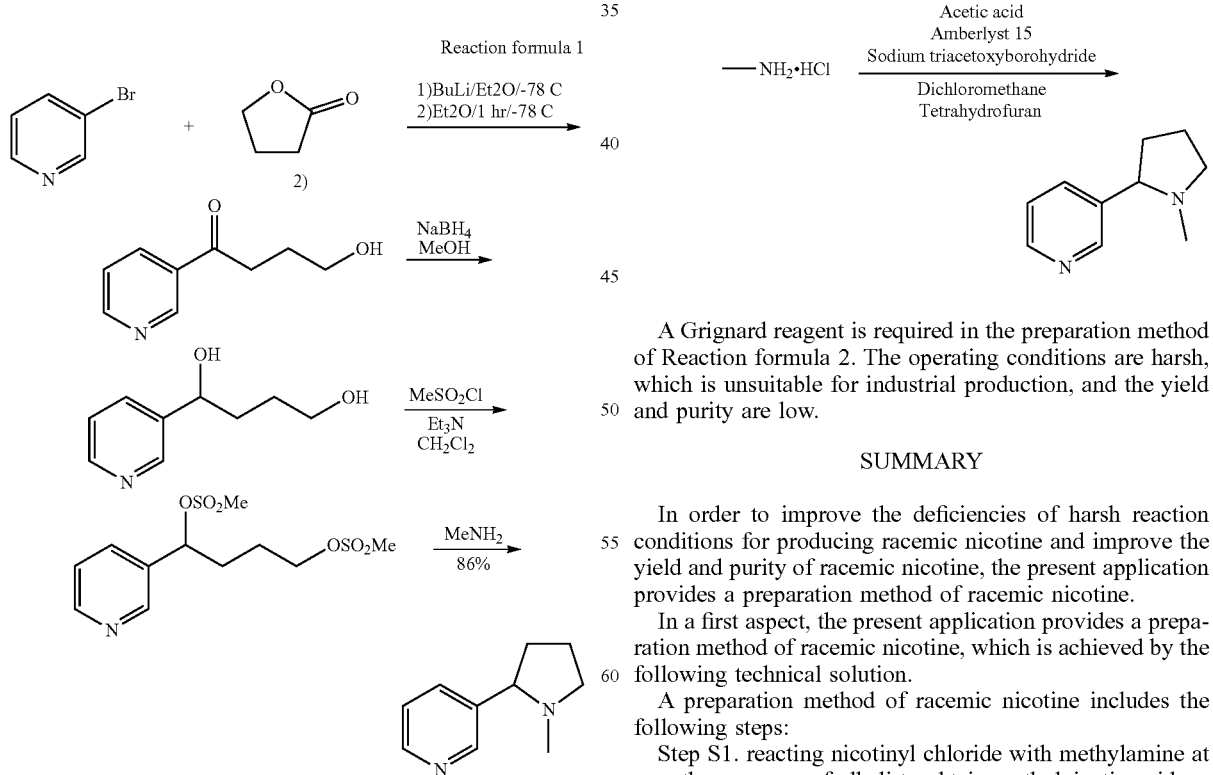

The preparation method of Reaction formula 1 uses expensive 3-bromopyridine as the starting material, and requires ultra-low temperature (−78° C.). The experimental conditions are harsh, so it is not suitable for industrial production.

A preparation method for synthesizing racemic nicotine from nicotinic acid as starting material is reported in the literature (Journal of the Chemical Society, Perkin transactions 1 (2002), (2), 143-154), as shown in Reaction formula 2:

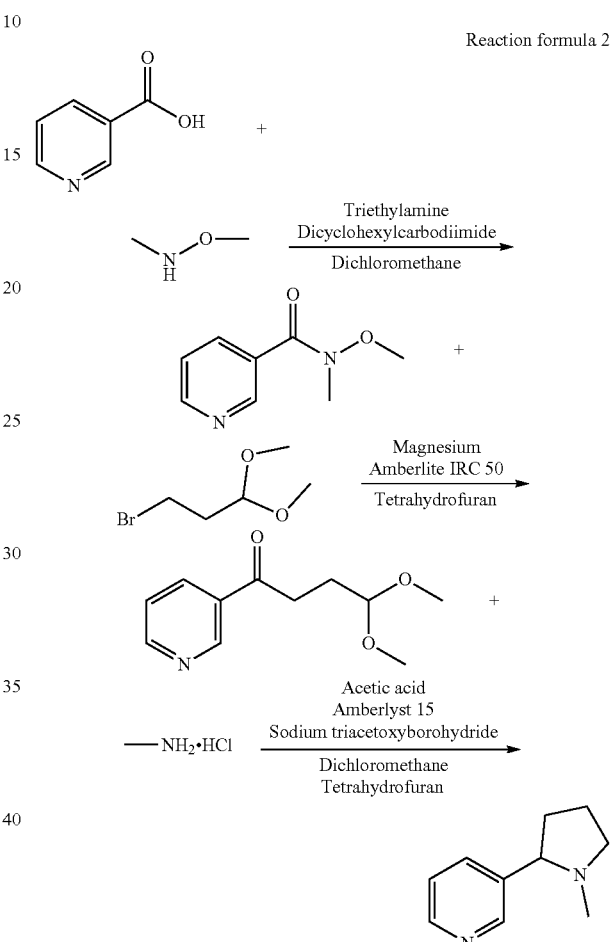

A Grignard reagent is required in the preparation method of Reaction formula 2. The operating conditions are harsh, which is unsuitable for industrial production, and the yield and purity are low.

SUMMARY

In order to improve the deficiencies of harsh reaction conditions for producing racemic nicotine and improve the yield and purity of racemic nicotine, the present application provides a preparation method of racemic nicotine.

In a first aspect, the present application provides a preparation method of racemic nicotine, which is achieved by the following technical solution.

A preparation method of racemic nicotine includes the following steps:
  Step S1. reacting nicotinyl chloride with methylamine at the presence of alkali to obtain methylnicotinamide;
  Step S2. condensing methylnicotinamide with chloroacetone at the presence of an organic base to obtain N-methyl-N-(2-oxpropyl)nicotinamide;

Step S3. self aldol condensing N-methyl-N-(2-oxpropyl) nicotinamide to obtain 1-methyl-5-(pyridin-3-yl)-1,2-dihydro-3H-pyrrol-3-one; and Step S4. reacting 1-methyl-5-(pyridin-3-yl)-1,2-dihydro-3H-pyrrol-3-one with a reducing agent to obtain a racemic nicotine.

In the above technical solution, nicotinyl chloride and methylamine are cheap and easily available raw materials. Nicotinyl chloride and methylamine are reacted under alkaline conditions to obtain methylnicotinamide, then condensed with monochloroacetone to obtain N-methyl-N-(2-oxopropyl) nicotinamide, then self aldol condensed to obtain 1-methyl-5-(pyridin-3-yl)-1,2-dihydro-3H-pyrrol-3-one, and finally reduced to obtain racemic nicotine. The present application uses nicotinyl chloride and methylamine as the starting raw materials, involving low cost, and thus provides a new route for the synthesis of racemic nicotine. The whole reaction involves in a short synthesis route, simple operation, mild reaction conditions, simple post-processing, and high yield of racemic nicotine, being suitable for large-scale industrial production.

Preferably, in Step S1, a molar ratio of nicotinyl chloride, methylamine and alkali is 1:(1.5-2.5):(3-5). More preferably, the molar ratio of nicotinyl chloride, methylamine and alkali is 1:2:4.

Preferably, in Step S1, the methylamine is any one selected from the group consisting of monomethylamine, methylamine hydrochloride, methylamine hydrobromide and methylamine hydroiodide. Preferably, the methylamine is methylamine hydrochloride.

Preferably, in Step S1, the alkali is any one selected from the group consisting of alkali metal alkoxide, alkaline-earth metal hydride, alkaline-earth metal oxide, amine, metal salt of amine, hydroxide, carbonate and bicarbonate.

In the present application, the alkali metal alkoxide includes, but not limited to, any one selected from the group consisting of sodium butoxide, sodium methoxide, sodium ethoxide and potassium tert-butoxide.

In the present application, the alkaline-earth metal hydride includes, but not limited to, one or more selected from the group consisting of NaH, LiH and KH.

In the present application, the alkaline-earth metal oxide includes, but not limited to, one or more selected from the group consisting of $Na_2O$, $Li_2O$ and $K_2O$.

In the present application, the amine is any one selected from the group consisting of N,N-Diisopropylethylamine, triethylamine and N, N-diethylethylamine. Preferably, the amine is N, N-Diisopropylethylamine or triethylamine.

In the present application, the metal salt of the amine includes, but not limited to, sodium bis(trimethylsilyl)amide and/or lithium diisopropylamide.

In the present application, the hydroxide includes, but not limited to, one or more selected from the group consisting of sodium hydroxide, lithium hydroxide and magnesium hydroxide.

In the present application, the carbonate includes, but not limited to, one or more selected from the group consisting of sodium carbonate, potassium carbonate and cesium carbonate.

In the present application, the bicarbonate includes, but not limited to, sodium bicarbonate and/or potassium bicarbonate.

Preferably, the alkali is amine or carbonate. Further preferably, the alkali is any one selected from the group consisting of N, N-Diisopropylethylamine, triethylamine and potassium carbonate.

In the present application, the solvents used in Step S1 include, but not limited to, tetrahydrofuran.

In the present application, a reaction temperature of Step S1 is 20-30° C. Preferably, the reaction temperature of Step S1 is 25° C.

In the present application, a reaction time of Step S1 is 2.5-3.5 h. Preferably, the reaction time of Step S1 is 3 h.

In the present application, in Step S1, after the reaction of nicotinyl chloride, methylamine and alkali, the system is adjusted to slightly acidic with acid, then extracted, and rotation evaporated to remove the solvent to obtain crude methylnicotinamide, which can be used directly in the next step without the need of purification. The pH of the system can be adjusted to 6 with 0.1 mol/L hydrochloric acid. Ethyl acetate can be used for extraction.

Preferably, in Step S2, a molar ratio of methylnicotinamide, monochloroacetone and organic base is 1:(1.1-2):(1.1-1.5). More preferably, the molar ratio of methylnicotinamide, monochloroacetone and organic base is 1:(1.1-1.3):(1.05-1.15). Most preferably, the molar ratio of methylnicotinamide, monochloroacetone and organic base is 1:1.2:1.1.

Preferably, in Step S2, the organic base is an amine or an alkali metal alkoxide. More preferably, the organic base is an amine.

Preferably, in Step S2, the amine is N, N-Diisopropylethylamine.

In the present application, the solvents used in Step S2 include, but not limited to, dichloroethane.

In the present application, a reaction temperature of Step S2 is 20-30° C. Preferably, the reaction temperature of Step S2 is 25° C.

In the present application, a reaction time of Step S2 is 4-6 h. Preferably, the reaction time of Step S2 is 5 h.

In the present application, in Step S2, after the reaction between methylnicotinamide and monochloroacetone, ethyl acetate can be used for extraction, and solvent can be removed from the organic phase to obtain crude N-methyl-N-(2-oxpropyl)nicotinamide, which can be directly used in the next reaction without the need of purification.

In the present application, the solvents used in Step S3 include, but not limited to, tetrahydrofuran.

In the present application, in Step S3, the self-aldol condensation reaction of the N-methyl-N-(2-oxpropyl)nicotinamide is carried out under alkaline conditions. The alkali used in the alkaline condition includes, but not limited to, any one selected from the group consisting of sodium hydroxide, potassium hydroxide, lithium hydroxide, magnesium hydroxide, cesium hydroxide and barium hydroxide. Preferably, the self-aldol condensation of N-methyl-N-(2-oxpropyl)nicotinamide is performed under the catalysis of sodium hydroxide.

In the present application, in Step S3, a molar ratio of N-methyl-N-(2-oxopropyl)nicotinamide to sodium hydroxide is 1:(1.2-1.7). Preferably, the molar ratio of N-methyl-N-(2-oxpropyl)nicotinamide to sodium hydroxide is 1:1.5.

In the present application, a reaction temperature of Step S3 is 20-30° C. Preferably, the reaction temperature of Step S3 is 25° C.

In the present application, a reaction time of Step S3 is 5-8 h. Preferably, the reaction time of Step S3 is 6 h.

In the present application, in Step S3, after the self-aldol condensation reaction of N-methyl-N-(2-oxpropyl)nicotinamide, the system is adjusted by adding acid to a neutral pH, then extracted, rotary evaporated to remove the solvent to obtain the crude 1-methyl-5-(pyridin-3-yl)-1,2-dihydro-3H-pyrrol-3-one, which can be used in next step without the need of purification.

In the present application, in Step S4, a molar ratio of the 1-methyl-5-(pyridin-3-yl)-1,2-dihydro-3H-pyrrol-3-one to the reducing agent is 1:(1-2). Preferably, the molar ratio of the 1-methyl-5-(pyridin-3-yl)-1,2-dihydro-3H-pyrrol-3-one to the reducing agent is 1:1.5.

Preferably, in Step S4, the reducing agent is one or more selected from the group consisting of metal borohydride, iron, zinc, hydrogen, ferrous chloride, zinc chloride, stannous chloride and lithium aluminum hydride.

In the present application, the metal borohydride includes, but not limited to, one or more selected from the group consisting of sodium borohydride, potassium borohydride and sodium cyanobohydride borane.

Preferably, in Step S4, the reducing agent is metal borohydride. More preferably, the reducing agent is sodium borohydride.

In the present application, the solvents used in Step S4 include, but not limited to, tetrahydrofuran.

In the present application, a reaction temperature of Step S4 is (−5)-5° C. Preferably, the reaction temperature of Step S4 is 0° C.

In the present application, a reaction time of Step S4 is 1-3 h. Preferably, the reaction time of Step S4 is 2 h.

In the present application, in Step S4, after 1-methyl-5-(pyridin-3-yl)-1,2-dihydro-3H-pyrrol-3-one is reduced by reducing agent, it can be extracted with ethyl acetate, and rotary evaporated to remove the solvent to obtain crude racemic nicotine, which is then refined and purified to obtain racemic nicotine.

In summary, the present application provides the beneficial effects as follow.

The present application uses cheap and easily available nicotinyl chloride and methylamine as starting materials, involving low material cost and providing a new route for synthesizing racemic nicotine. Nicotinyl chloride and methylamine are reacted under alkaline conditions to obtain methylnicotinamide, then condensed with monochloroacetone to obtain N-methyl-N-(2-oxopropyl) nicotinamide, then self-aldol condensed to obtain 1-methyl-5-(pyridin-3-yl)-1,2-dihydro-3H-pyrrol-3-one, and finally reduced to obtain racemic nicotine. The whole reaction involves in a short synthesis route, simple operation, mild reaction conditions, simple post-processing, high yield of racemic nicotine, being suitable for large-scale industrial production.

DESCRIPTION OF THE EMBODIMENTS

Further details of this present application are given below in combination with examples.

All the raw materials used in the present application can be obtained through commercial sale. The raw materials not mentioned in various examples and comparative examples of the present application are purchased from Sinopharm Chemical Reagent Co., Ltd unless otherwise specified.

EXAMPLES

Examples 1-14 provide a preparation method of racemic nicotine, which is described below with Example 1 as an example.

The preparation method of racemic nicotine provided in Example 1, in which methylamine is methylamine hydrochloride, and its synthetic route is shown in Reaction formula 3:

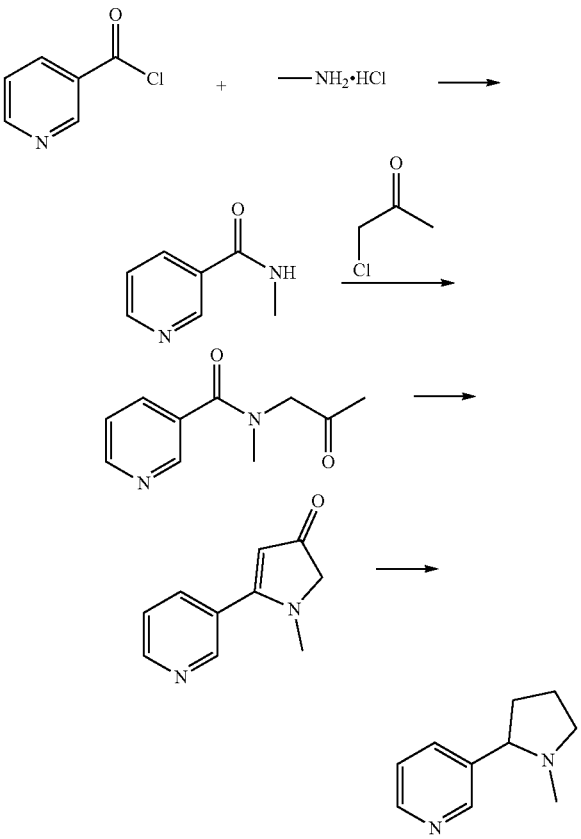

Reaction formula 3

The specific preparation steps were as follow.

Step S1. 0.142 g (0.001 mol, 1 eq) nicotinyl chloride and 0.135 g (0.002 mol, 2 eq) methylamine hydrochloride were added to 100 mL tetrahydrofuran at 25° C., then added with 0.517 g (0.004 mol, 4 eq) N,N-Diisopropylethylamine, and reacted at 25° C. at a stirring speed of 400 rpm for 3 h. After the reaction, the system was adjusted to pH value of 7 with 0.1 mol/L hydrochloric acid, and extracted with 200 mL ethyl acetate-water (the volume ratio of ethyl acetate to water is 2:1) to obtain an organic phase, from which the solvent was removed by rotatory evaporation to obtain crude methylnicotinamide.

Step S2. The crude methylnicotinamide obtained in Step S1 was added to 100 mL dichloroethane at 25° C., added with 0.111 g (0.0012 mol, 1.2 eq) of monochloroacetone and then 0.142 g (0.0011 mol, 1.1 eq) of N, N-Diisopropylethylamine, reacted at 25° C. at a stirring speed of 400 rpm for 5 h, and after the reaction, extracted with 200 mL of ethyl acetate-water (the volume ratio of ethyl acetate to water is 2:1), to obtain an organic phase, from which the solvent was removed by rotatory evaporation to obtain crude N-methyl-N-(2-oxopropyl)nicotinamide.

Step S3. The crude N-methyl-N-(2-oxpropyl)nicotinamide obtained in Step S2 was dissolved in 100 mL tetrahydrofuran at 25° C., added with 0.06 g (0.0015 mol, 1.5 eq) NaOH, and reacted at 25° C. at the stirring speed of 400 rpm for 6 h. After the reaction, the system was adjusted to pH value of 7 with 0.1 mol/L hydrochloric acid, and extracted with 200 mL ethyl acetate-water (the volume ratio of ethyl acetate to water is 2:1), to obtain an organic phase, from which the solvent was removed by rotary evaporation to obtain crude 1-methyl-5-(pyridin-3-yl)-1,2-dihydro-3H-pyrrol-3-one.

Step S4. The crude 1-methyl-5-(pyridin-3-yl)-1,2-dihydro-3H-pyrrol-3-one obtained in Step S3 was dissolved in 100 mL tetrahydrofuran at 0° C., added with 0.057 g (0.0015 mol, 1.5 eq) sodium borohydride, reacted at 0° C. for 2 h to reduce 1-methyl-5-(pyridin-3-yl)-1,2-dihydro-3H-pyrrol-3-one to racemic nicotine, and then extracted with 200 mL ethyl acetate-water (the volume ratio of ethyl acetate to water is 2:1), to obtain an organic phase, from which the solvent was removed by rotary evaporation to obtain crude racemic nicotine. Finally, the crude racemic nicotine was subjected to atmospheric distillation for once and refining to obtain racemic nicotine, with a yield of 76%.

It should be noted that each mass and specific molar amount in the example in the present application can be selected according to the size of the industrialized container, as long as the equivalence ratio between individual reaction raw materials is kept consistent.

Examples 2-5 differ from Example 1 only by varied use amount of methylamine hydrochloride and N,N-Diisopropylethylamine in Step S1, as shown in Table 1.

TABLE 1

Effect of the use amount of methylamine hydrochloride and N,N-Diisopropylethylamine on the reaction in Step S1

| Number | Equivalent quantity of methylamine hydrochloride (eq) | Equivalent quantity of N,N-Diisopropylethylamine (eq) | Yield of racemic nicotine (%) |
|---|---|---|---|
| Example 1 | 2 | 4 | 76 |
| Example 2 | 1.5 | 4 | 60 |
| Example 3 | 2.5 | 4 | 68 |
| Example 4 | 2 | 3 | 63 |
| Example 5 | 2 | 5 | 75 |

Examples 6-7 differ from Example 1 only by the types of alkali used in Step S1, as shown in Table 2.

TABLE 2

Effect of the selected alkali on reaction in Step S1

| Number | Selected Alkali | Yield of racemic nicotine (%) |
|---|---|---|
| Example 1 | N,N-Diisopropylethylamine | 76 |
| Example 6 | Triethylamine | 74 |
| Example 7 | Potassium carbonate | 70 |

Example 8 differs from Example 1 only by the type of methylamine used in Step S1, as shown in Table 3.

TABLE 3

Effect of selected methylamine on reaction in Step S1

| Number | Selected Methylamine | Yield of racemic nicotine (%) |
|---|---|---|
| Example 1 | Methylamine hydrochloride | 76 |
| Example 8 | Methylamine hydrobromide | 73 |

Examples 9-12 differ from Example 1 only by the use amount of monochloroacetone and N,N-Diisopropylethylamine in Step S2, as shown in Table 4.

TABLE 4

Effect of the use amount of monochloroacetone and N,N-Diisopropylethylamine on the reaction in Step S2

| Number | Equivalent quantity of Chloroacetone (eq) | Equivalent quantity of N,N-Diisopropylethylamine (eq) | Yield of racemic nicotine (%) |
|---|---|---|---|
| Example 1 | 1.2 | 1.1 | 76 |
| Example 9 | 1.1 | 1.1 | 68 |
| Example 10 | 1.3 | 1.1 | 74 |
| Example 11 | 1.2 | 1.05 | 70 |
| Example 12 | 1.2 | 1.15 | 74 |

Examples 13-14 differ from Example 1 only by the types of organic base used in Step S2 reaction, as shown in Table 5.

TABLE 5

Effect of selected alkali on reaction in Step S2

| Number | Selected Organic base | Yield of racemic nicotine (%) |
|---|---|---|
| Example 1 | N,N-Diisopropylethylamine | 76 |
| Example 13 | N•N-diethylethylamine | 66 |
| Example 14 | Sodium tert-butoxide | 74 |

The specific examples represent only an explanation of the present application, imposing no limitation to the present application. Modifications can be made to these examples without creative contribution as needed after reading this specification, but they are protected by the patent law as long as they are within the scope of the claims of the present application.

What is claimed is:

1. A preparation method of a racemic nicotine, comprising the following steps:
    step S1, reacting nicotinyl chloride with methylamine at the presence of an alkali to obtain methylnicotinamide;
    step S2, condensing methylnicotinamide with chloroacetone at the presence of an organic base to obtain N-methyl-N-(2-oxpropyl)nicotinamide;
    step S3, self-aldol condensing N-methyl-N-(2-oxpropyl) nicotinamide to obtain 1-methyl-5-(pyridin-3-yl)-1,2-dihydro-3H-pyrrol-3-one; and
    step S4, reacting 1-methyl-5-(pyridin-3-yl)-1,2-dihydro-3H-pyrrol-3-one with a reducing agent to obtain the racemic nicotine.

2. The preparation method of the racemic nicotine according to claim 1, wherein, in the step S1, a molar ratio of nicotinyl chloride, methylamine and the alkali is 1:(1.5-2.5):(3-5).

3. The preparation method of the racemic nicotine according to claim 1, wherein, in the step S1, the methylamine is any one selected from the group consisting of monomethylamine, methylamine hydrochloride, methylamine hydrobromide and methylamine hydroiodide.

4. The preparation method of the racemic nicotine according to claim 1, wherein, in the step S1, the alkali is any one selected from the group consisting of alkali metal alkoxide, alkaline-earth metal hydride, alkaline-earth metal oxide, amine, metal salts of amine, hydroxide, carbonate and bicarbonate.

5. The preparation method of the racemic nicotine according to claim 4, wherein, the amine is any one selected from the group consisting of N,N-Diisopropylethylamine, triethylamine and N,N-diethylethylamine.

6. The preparation method of the racemic nicotine according to claim 1, wherein, in the step S2, a molar ratio of methylnicotinamide, monochloroacetone and the organic base is 1:(1.1-2):(1.1-1.5).

7. The preparation method of the racemic nicotine according to claim 6, wherein, the molar ratio of methylnicotinamide, monochloroacetone and the organic base is 1:1.2:1.1.

8. The preparation method of the racemic nicotine according to claim 1, wherein, in the step S2, the organic base is one selected from the group consisting of amine and alkali metal alkoxide.

9. The preparation method of the racemic nicotine according to claim 8, wherein, in the step S2, the amine is N,N-Diisopropylethylamine.

10. The preparation method of the racemic nicotine according to claim 1, wherein, in the step S4, the reducing agent is one or more selected from the group consisting of metal borohydride, iron, zinc, hydrogen, ferrous chloride, zinc chloride, stannous chloride and lithium aluminum hydride.

* * * * *